(12) United States Patent
Bouyssou et al.

(10) Patent No.: US 7,244,728 B2
(45) Date of Patent: Jul. 17, 2007

(54) LONG ACTING BETAMIMETICS FOR THE TREATMENT OF RESPIRATORY DISEASES

(75) Inventors: Thierry Bouyssou, Mietingen (DE); Christoph Hoenke, Ingelheim (DE); Ingo Konetzki, Warthausen (DE); Andreas Schnapp, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 177 days.

(21) Appl. No.: 11/074,263

(22) Filed: Mar. 7, 2005

(65) Prior Publication Data
US 2005/0209227 A1    Sep. 22, 2005

Related U.S. Application Data

(60) Provisional application No. 60/562,572, filed on Apr. 15, 2004.

(30) Foreign Application Priority Data
Mar. 17, 2004    (EP) ................... 04006348

(51) Int. Cl.
*C07D 265/36*    (2006.01)
*A61K 31/538*    (2006.01)

(52) U.S. Cl. .................... 514/230.5; 544/105

(58) Field of Classification Search ............. 514/230.5; 544/105
See application file for complete search history.

(56) References Cited

U.S. PATENT DOCUMENTS 4,460,581 A    7/1984    Fuegner et al.

2002/0022625 A1    2/2002    Schromm et al.
2004/0010003 A1    1/2004    Banholzer et al.

FOREIGN PATENT DOCUMENTS

WO    WO 01/83462    11/2001
WO    WO 03/087097    10/2003

OTHER PUBLICATIONS

R. S. Bedi Indian J. Chest Dis. Allied Sci. 2005; 47:243-244.*

* cited by examiner

*Primary Examiner*—Kahsay Habte
(74) *Attorney, Agent, or Firm*—Michael P. Morris; Mary-Ellen M. Devlin; Timothy X. Witkowski

(57) ABSTRACT

The present invention relates to the compounds of general formula 1

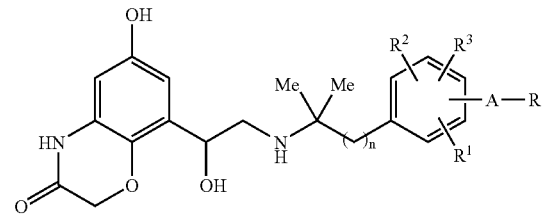

wherein the groups R, R1, R2, R3 and A may have the meanings given in the claims and specification, processes for preparing them and their use as medicaments, particularly for the treatment of inflammatory and obstructive respiratory complaints.

16 Claims, No Drawings

LONG ACTING BETAMIMETICS FOR THE TREATMENT OF RESPIRATORY DISEASES

RELATED APPLICATIONS

Benefit of U.S. Provisional Application Ser. No. 60/562,572, filed on Apr. 15, 2004, is hereby claimed, and which application is incorporated herein in its entirety.

FIELD OF THE INVENTION

The present invention relates to the compounds of general formula 1

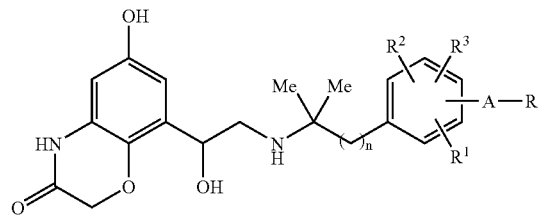

wherein the groups R, R1, R2, R3 and A may have the meanings given in the claims and specification, processes for preparing them and their use as medicaments, particularly for the treatment of inflammatory and obstructive respiratory complaints.

BACKGROUND TO THE INVENTION

Betamimetics (β-adrenergic substances) are known from the prior art. Reference may be made for example to the disclosure of U.S. Pat. No. 4,460,581 which proposes betamimetics for the treatment of a variety of diseases.

For drug treatment of diseases it is often desirable to prepare medicaments with a longer duration of activity. As a rule, this ensures that the concentration of the active substance in the body needed to achieve the therapeutic effect is present over a longer period of time without the need to administer the drug repeatedly, frequently. The administration of an active substance at longer intervals of time also contributes considerably to the patient's wellbeing.

The aim of the present invention is therefore to provide betamimetics which deliver a therapeutic benefit on the one hand in the treatment of inflammatory and obstructive respiratory complaints, most preferably in the treatment of asthma or COPD and are further characterised by a longer duration of activity and can thus be used to prepare pharmaceutical compositions with a longer duration of activity. In addition to the above objectives, the present invention also sets out to provide betamimetics which are not only exceptionally potent but are also characterised by a high degree of selectivity with respect to the $\beta_2$-adreno-receptor.

DETAILED DESCRIPTION OF THE INVENTION

Surprisingly it has been found that the abovementioned problems are solved by compounds of general formula 1.

Accordingly, the present invention relates to compounds of general formula 1

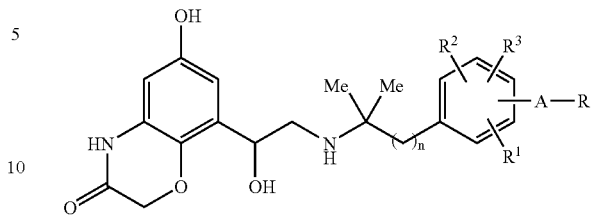

wherein
n denotes 1 or 2, preferably 1;
A denotes oxygen or a single bond;
R denotes —$C_1$-$C_6$-alkyl, which is mono- or polysubstituted by one or more halogen atoms;
$R^1$, $R^2$ and $R^3$ which may be identical or different denote hydrogen, $C_1$-$C_6$-alkyl, halogen-$C_1$-$C_6$-alkylene, OH, HO—$C_{1-6}$-alkylene, —O—$C_1$-$C_6$-alkyl, $C_6$-$C_{10}$-aryl, $C_6$-$C_{10}$-aryl-$C_1$-$C_4$-alkylene, $C_6$-$C_{10}$-aryl-$C_1$-$C_6$-alkylene-O, —COOH,
—COO$C_1$-$C_6$-alkyl, —O—$C_1$-$C_6$-alkylene-COOH,
—O—$C_1$-$C_6$-alkylene-COO$C_1$-$C_6$-alkyl, —NHSO$_3$H,
—NHSO$_2$—$C_1$-$C_6$-alkyl, CN, NH$_2$, —NH—$C_1$-$C_6$-alkyl, —N($C_1$-$C_6$-alkyl)$_2$, NO$_2$, —S—$C_1$-$C_6$-alkyl,
—SO$_2$—$C_1$-$C_6$-alkyl, —SO—$C_1$-$C_6$-alkyl, —O(CO)$C_1$-$C_6$-alkyl, —CO$C_1$-$C_6$-alkyl,
—NHCO$C_1$-$C_6$-alkyl or halogen.

Preferred compounds of general formula 1 are those wherein
n denotes 1 or 2, preferably 1,
A denotes oxygen or a single bond;
R denotes $C_1$-$C_4$-alkyl, which is mono- or polysubstituted, preferably mono- to trisubstituted, by one or more halogen atoms, preferably by fluorine or chlorine;
$R^1$, $R^2$ and $R^3$ which may be identical or different denote hydrogen, $C_1$-$C_4$-alkyl, halogen-$C_1$-$C_4$-alkylene, OH, HO—$C_1$-$C_4$-alkylene, —O—$C_1$-$C_4$-alkyl, phenyl, phenyl-$C_1$-$C_4$-alkylene, phenyl-$C_1$-$C_4$-alkylene-O, —COOH, —COO$C_1$-$C_4$-alkyl,
—O—$C_1$-$C_4$-alkylene-COOH, —O—$C_1$-$C_4$-alkylene-COO$C_1$-$C_4$-alkyl,
—NHSO$_2$—$C_1$-$C_4$-alkyl, CN, NH$_2$, —NH—$C_1$-$C_4$-alkyl, —N($C_1$-$C_4$-alkyl)$_2$, NO$_2$,
—S—$C_1$-$C_4$-alkyl, —SO$_2$—$C_1$-$C_4$-alkyl, —SO—$C_1$-$C_4$-alkyl, —O(CO)$C_1$-$C_4$-alkyl,
—CO$C_1$-$C_4$-alkyl, —NHCO$C_1$-$C_4$-alkyl or halogen.

Also preferred are compounds of general formula 1 wherein
n denotes 1 or 2, preferably 1,
A denotes oxygen or a single bond;
R denotes a methyl or ethyl group which is mono-, di- or trisubstituted by one or more halogen atoms selected from fluorine or chlorine;
$R^1$ and $R^2$ which may be identical or different, preferably identical, denote hydrogen, halogen, $C_1$-$C_4$-alkyl or —O—$C_1$-$C_4$-alkyl;
$R^3$ denotes hydrogen, $C_1$-$C_4$-alkyl, OH, halogen, —O—$C_1$-$C_4$-alkyl, halogen-$C_1$-$C_4$-alkylene, —O—$C_1$-$C_4$-alkylene-COOH, —O—$C_1$-$C_4$-alkylene-CO—O—$C_1$-$C_4$-alkyl.

Preferred compounds of general formula 1 are those wherein
n denotes 1;
A denotes oxygen or a single bond, preferably a single bond;
R denotes —$CH_2$—$CH_2Cl$, —$CH_2CCl_3$, —$CHCl$—$CCl_3$, —$CCl_3$, —$CH_2Cl$, —$CHCl_2$, —$CH_2CF_3$, —$CHF$—$CF_3$, —$CF_3$, —$CH_2F$, —$CH_2$—$CH_2F$ or —$CHF_2$;
$R^1$ and $R^2$ which may be identical or different, preferably identical, denote hydrogen, fluorine, chlorine, methyl or methoxy;
$R^3$ denotes hydrogen, $C_1$-$C_4$-alkyl, OH, fluorine, chlorine, bromine, —O—$C_1$-$C_4$-alkyl, —$CF_3$, —O—$C_1$-$C_4$-alkylene-COOH, —O—$C_1$-$C_4$-alkylene-CO—O—$C_1$-$C_4$-alkyl.

Particularly preferred compounds of general formula 1 are those wherein
n denotes 1;
A denotes oxygen or a single bond, preferably a single bond;
R denotes —$CH_2CF_3$, —$CHF$—$CF_3$, —$CF_3$, —$CH_2F$, —$CH_2$—$CH_2F$ or —$CHF_2$;
$R^1$ and $R^2$ which may be identical or different, preferably identical, denote hydrogen, fluorine, chlorine, methyl or ethyl;
$R^3$ denotes hydrogen, fluorine, chlorine, methyl, ethyl, OH, methoxy, ethoxy, —$CF_3$, —O—$CH_2$—COOH, —O—$CH_2$—COOmethyl or —O—$CH_2$—COOethyl.

Also particularly preferred are the above-mentioned compounds of general formula 1 wherein $R^1$ and $R^2$ denote hydrogen and the groups A, R and $R^3$ may have the meanings given above.

Also particularly preferred are the above-mentioned compounds of general formula 1 wherein A denotes a single bond and the groups R, $R^1$, $R^2$ and $R^3$ may have the meanings given above.

Also particularly preferred are the above-mentioned compounds of general formula 1 wherein $R^3$ denotes hydrogen, fluorine, chlorine, methyl, ethyl, OH, methoxy or ethoxy, preferably hydrogen, fluorine or chlorine, particularly preferably hydrogen and the groups A, R, $R^1$ and $R^2$ may have the meanings given above.

Also particularly preferred are the above-mentioned compounds of general formula 1 wherein R denotes —$CF_3$, —$CH_2F$ or —$CHF_2$, preferably —$CF_3$ and the groups A, $R^1$, $R^2$ and $R^3$ may have the meanings given above.

Also particularly preferred are compounds of general formula 1 selected from the group comprising
8-{2-[2-(4-fluoro-3-trifluoromethyl-phenyl)-1,1-dimethyl-ethylamino]-1-hydroxy-ethyl}-6-hydroxy-4H-benzo[1,4]oxazin-3-one;
8-{2-[1,1-dimethyl-2-(4-trifluoromethyl-phenyl)-ethylamino]-1-hydroxy-ethyl}-6-hydroxy-4H-benzo[1,4]oxazin-3-one;
8-{2-[1,1-dimethyl-2-(3-trifluomethyl-phenyl)-ethylamino]-1-hydroxy-ethyl}-6-hydroxy-4H-benzo[1,4]oxazin-3-one;
8-{2-[1,1-dimethyl-2-(4-trifluoromethoxy-phenyl)-ethylamino]-1-hydroxy-ethyl}-6-hydroxy-4H-benzo[1,4]oxazin-3-one;
8-{2-[2-(4-chloro-3-trifluoromethyl-phenyl)-1,1-dimethyl-ethylamine]-1-hydroxy-ethyl}-6-hydroxy-4H-benzo[1,4]oxazin-3-one;
8-{2-[1,1-dimethyl-2-(2-trifluoromethyl-phenyl)-ethylamino]-1-hydroxy-ethyl}-6-hydroxy-4H-benzo[1,4]oxazin-3-one;
8-{2-[2-(3,5-bis-trifluoromethyl-phenyl)-1,1-dimethyl-ethylamino]-1-hydroxy-ethyl}-6-hydroxy-4H-benzo[1,4]oxazin-3-one.

In another aspect the present invention relates to the abovementioned new compounds of formula 1 in the form of the individual optical isomers, mixtures of the individual enantiomers or racemates. Particularly preferred are compounds of formula 1 in the form of the enantiomerically pure compounds, while the R-enantiomers of the compounds of formula 1 are of exceptional importance according to the invention. Methods of separating racemates into the respective enantiomers are known in the prior art and may be used analogously to prepare the enantiomerically pure R- and S-enantiomers of the compounds of formula 1.

In another aspect the present invention relates to the abovementioned compounds of formula 1 in the form of the acid addition salts with pharmacologically acceptable acids as well as optionally in the form of the solvates and/or hydrates thereof. By acid addition salts with pharmacologically acceptable acids are meant, for example, the salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

Of the abovementioned acid addition salts the salts of hydrochloric acid, methanesulphonic acid, benzoic acid and acetic acid are particularly preferred according to the invention.

In another aspect the present invention relates to the abovementioned compounds of formula 1 for use as pharmaceutical compositions. The present invention further relates to the use of the abovementioned new compounds of general formula 1 for preparing a pharmaceutical composition for the treatment of inflammatory and obstructive respiratory complaints, most preferably in the treatment of asthma or COPD. The present invention further relates to the use of the abovementioned new compounds of general formula 1 for preparing a pharmaceutical composition for the once- or twice-a-day treatment of inflammatory and obstructive respiratory complaints, most preferably asthma or COPD.

Moreover the present invention relates to a process for the treatment of inflammatory and obstructive respiratory complaints, particularly preferably for the treatment of asthma or COPD., characterised in that one or more one or more of the abovementioned compounds of general formula 1 are administered once a day in therapeutically effective amounts.

For use according to the invention the compounds of general formula 1 may optionally be used in the form of their individual optical isomers, mixtures of the individual enantiomers or racemates. If the compounds are used in enantiomerically pure form, the R-enantiomers are preferred.

Unless otherwise stated, the alkyl groups are straight-chained or branched alkyl groups having 1 to 4 carbon atoms. The following are mentioned by way of example: methyl, ethyl, propyl or butyl. In some cases the abbreviations Me, Et, Prop or Bu are used to denote the groups methyl, ethyl, propyl or butyl. Unless otherwise stated, the definitions propyl and butyl include all the possible isomeric forms of the groups in question. Thus, for example, propyl includes n-propyl and iso-propyl, butyl includes iso-butyl, sec.butyl and tert.-butyl, etc.

Unless otherwise stated, the alkylene groups are branched and unbranched double-bonded alkyl bridges having 1 to 4 carbon atoms. The following are mentioned by way of example: methylene, ethylene, n-propylene or n-butylene.

Unless otherwise stated, the term alkyloxy groups (or —O-alkyl groups) denotes branched and unbranched alkyl groups having 1 to 4 carbon atoms which are linked via an oxygen atom. Examples of these include: methyloxy, ethyloxy, propyloxy or butyloxy. The abbreviations MeO—, EtO—, PropO— or BuO— are used in some cases to denote the groups methyloxy, ethyloxy, propyloxy or butyloxy. Unless otherwise stated, the definitions propyloxy and butyloxy include all possible isomeric forms of the groups in question. Thus, for example, propyloxy includes n-propyloxy and iso-propyloxy, butyloxy includes iso-butyloxy, sec.butyloxy and tert.-butyloxy, etc. In some cases, within the scope of the present invention, the term alkoxy is used instead of the term alkyloxy. Accordingly, the terms methoxy, ethoxy, propoxy or butoxy may also be used to denote the groups methyloxy, ethyloxy, propyloxy or butyloxy.

Halogen within the scope of the present invention denotes fluorine, chlorine, bromine or iodine. Unless stated otherwise, fluorine, chlorine and bromine are the preferred halogens, fluorine being particularly preferred.

Unless otherwise stated, aryl denotes an aromatic ring system with 6 to 10 carbon atoms. Preferred aryl groups within the scope of the present invention are phenyl and naphthyl.

Halo-alkylene, unless otherwise stated, denotes branched or unbranched alkyl groups which are substituted by at least one, possibly several halogen atoms. HO-alkylene, unless otherwise stated, denotes branched or unbranched alkyl groups which are substituted by OH. Aryl-alkylene, unless otherwise stated, denotes branched or unbranched alkyl groups which are substituted by an aryl group. Examples of preferred aryl-alkylene groups according to the invention are benzyl, phenylethyl, naphthylmethyl, naphthylethyl, while benzyl and phenylethyl are particularly preferred according to the invention.

The compounds according to the invention may be prepared analogously to methods already known from the prior art. Suitable methods of preparation are known for example from U.S. Pat. No. 4,460,581, which is incorporated herein by reference at this point.

The Examples described below serve to illustrate compounds known from the prior art, which may surprisingly be used according to the present invention for the treatment of COPD.

EXAMPLE 1

8-{2-[2-(4-fluoro-3-trifluoromethyl-phenyl)-1,1-dimethyl-ethylamino]-1-hydroxy-ethyl}-6-hydroxy-4H-benzo[1,4]oxazin-3-one

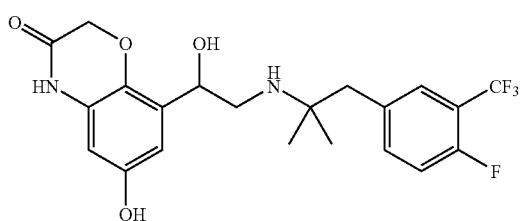

a) 1-(4-fluoro-3-trifluoromethyl-phenyl)-2-methyl-propan-1-ol

A Grignard is prepared from 10 g (40 mmol) 5-bromo-2-fluorobenzotrifluoride, dissolved in 50 mL diethyl ether, and 0.97 g (40 mmol) magnesium. Then a solution of 3.63 mL (40 mmol) isobutyraldehyde and 30 mL diethyl ether is added dropwise at ambient temperature and the mixture is left overnight with stirring. The reaction mixture is poured onto ice water, combined with 30 mL 20% sulphuric acid and extracted with diethyl ether. The combined organic phases are washed successively with sodium hydrogen carbonate solution, water and sodium chloride solution, dried with sodium sulphate and evaporated down. The chromatographic purification of the residue yields the target compound in the form of a brown oil.

Yield: 4.3 g (46%); mass spectroscopy: $[M]^+=236$.

b) 1-fluoro-4-(2-methyl-propenyl)-2-trifluoromethyl-benzene 4.3 g (18.2 mmol) 1-(4-fluoro-3-trifluoromethyl-phenyl)-2-methyl-propan-1-ol and 1.0 g (5.3 mmol) p-toluenesulphonic acid monohydrate in 100 mL toluene are refluxed for 3 hours using the water separator. Then the reaction mixture is combined with water and made alkaline with 1 N sodium hydroxide solution. After separation of the organic phase this is washed with water, dried with sodium sulphate and evaporated down. The oil remaining is further reacted directly.

Yield: 3.47 g; mass spectroscopy: $[M]^+=218$.

c) N-[2-(4-fluoro-3-trifluoromethyl-phenyl)-1,1-dimethyl-ethyl]-formamide

A solution of 30 mL conc. sulphuric acid and 15 mL glacial acetic acid is added dropwise to 1.0 g (20.4 mmol) sodium cyanide in 15 mL glacial acetic acid, while the temperature rises to approx. 30° C. Then 3.4 g (15.6 mmol) 1-fluoro-4-(2-methyl-propenyl)-2-trifluoromethyl-benzene, dissolved in 15 mL glacial acetic acid, are added and the mixture is stirred for 1 hour at 50-60° C. After cooling to ambient temperature the mixture is poured onto ice water and made alkaline with sodium hydroxide solution. It is extracted with diethyl ether and the organic phases are washed with water, dried with sodium sulphate and evaporated down. 3.64 g of a brown oil are obtained.

Mass spectroscopy: $[M+H]^+=264$.

d) 2-(4-fluoro-3-trifluoromethyl-phenyl)-1,1-dimethyl-ethylamine 3.30 g (12.5 mmol) N-[2-(4-fluoro-3-trifluoromethyl-phenyl)-1,1-dimethyl-ethyl]-formamide are combined with 25 mL water and 25 mL conc. hydrochloric acid and refluxed for 2 hours. The reaction mixture is diluted with water, made alkaline with potassium carbonate solution and extracted with dichloromethane. The combined organic phases are dried with sodium sulphate and freed from solvent. Brown oil.

Yield: 2.8 g (95%); mass spectroscopy: $[M+H]^+=236$.

e) 8-{2-[2-(4-fluoro-3-trifluoromethyl-phenyl)-1,1-dimethyl-ethylamino]-1-hydroxy-ethyl}-6-hydroxy-4H-benzo[1,4]oxazin-3-one 357 mg (1 mmol) 6-benzyloxy-8-(2-ethoxy-2-hydroxy-acetyl)-4H-benzo[1,4]oxazin-3-one and 235 mg (1 mmol) 2-(4-fluoro-3-trifluoromethyl-phenyl)-1,1-dimethyl-ethylamine are reacted analogously to the method described for Example 2c). Beige solid.

Yield: 265 mg (48%, trifluoroacetate); mass spectroscopy: [M+H]⁺=443.

EXAMPLE 2

8-{2-[1,1-dimethyl-2-(4-trifluoromethyl-phenyl)-ethylamino]-1-hydroxy-ethyl}-6-hydroxy-4H-benzo[1,4]oxazin-3-one

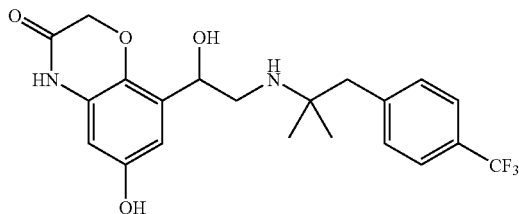

a) N-[1,1-dimethyl-2-(4-trifluoromethyl-phenyl)-ethyl]-formamide 4.2 g (19 mmol) 2-methyl-1-(4-trifluoromethyl-phenyl)-propanol-2-ol, obtained by reacting ethyl (4-trifluoromethyl-phenyl)-acetate with methylmagnesium bromide, are reacted and worked up using the method described for Example 1c). Yield: 4.6 g (98%).

b) 1,1-dimethyl-2-(4-trifluoromethyl-phenyl)-ethylamine

Obtained from 4.6 g (19 mmol) N-[1,1-dimethyl-2-(4-trifluoromethyl-phenyl)-ethyl]-formamide analogously to the method described for Example 1d).

Yield: 3.8 g (93%); mass spectroscopy: [M+H]⁺=218.

c) 8-{2-[1,1-dimethyl-2-(4-trifluoromethyl-phenyl)-ethylamino]-1-hydroxy-ethyl}-6-hydroxy-4H-benzo[1,4]oxazin-3-one 357 mg (1 mmol) 6-benzyloxy-8-(2-ethoxy-2-hydroxy-acetyl)-4H-benzo[1,4]oxazin-3-one and 217 mg (1 mmol) 1,1-dimethyl-2-(4-trifluoromethyl-phenyl)-ethylamine are stirred in 5 mL tetrahydrofuran at ambient temperature for 30 minutes. The mixture is cooled to 0° C. and under an argon atmosphere 1.5 mL of a 2 molar solution of lithium borohydride in tetrahydrofuran is added dropwise. The mixture is stirred for 30 min at ambient temperature, combined with 10 mL dichloromethane and 3 mL water, stirred for a further hour and then filtered through kieselguhr. The mixture is eluted with dichloromethane and the solvents are distilled off. The residue is dissolved in methanol and hydrogenated at 2.5 bar and ambient temperature with palladium on charcoal (10%) as catalyst. The catalyst is separated off and the crude product is purified by chromatography (reverse phase, acetonitrile/water gradient with 0.1% trifluoroacetic acid). Beige solid.

Yield: 212 mg (39%, trifluoroacetate); mass spectroscopy: [M+H]⁺=425.

EXAMPLE 3

8-{2-[1,1-dimethyl-2-(3-trifluomethyl-phenyl)-ethylamino]-1-hydroxy-ethyl}-6-hydroxy-4H-benzo[1,4]oxazin-3-one

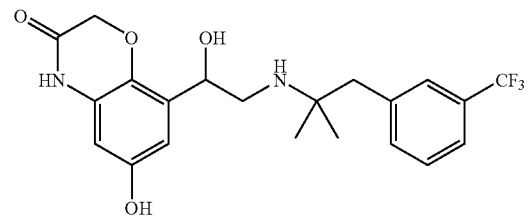

a) 2-methyl-1-(3-trifluoromethyl-phenyl)-propan-2-ol 90 mL of a 3 molar solution of methylmagnesium bromide in diethyl ether are diluted with 300 mL THF and cooled to −50° C. At this temperature 20 g 1-(3-trifluoromethyl-phenyl)-propan-2-one, dissolved in 100 mL THF, are added dropwise. After the addition has ended the reaction mixture is stirred overnight while heating to ambient temperature. It is combined with ammonium chloride solution and extracted with diethyl ether. The combined organic phases are washed with sodium chloride solution, dried with sodium sulphate and evaporated down. The residue remaining is purified by chromatography.

Yield: 9.5 g (44%).

b) N-[1,1-dimethyl-2-(3-trifluoromethyl-phenyl)-ethyl]-formamide 9.5 g (44 mmol) 2-methyl-1-(3-trifluoromethyl-phenyl)-propan-2-ol are reacted in a Ritter reaction analogously to the method described for Example 1c). Yellow oil.

Yield: 9.8 g (92%); mass spectroscopy: [M+H]⁺=246.

c) 1,1-dimethyl-2-(3-trifluoromethyl-phenyl)-ethylamine 9.8 g (40 mmol) N-[1,1-dimethyl-2-(3-trifluoromethyl-phenyl)-ethyl]-formamide are dissolved in 110 mL ethanol, combined with 200 ml of conc. hydrochloric acid and refluxed overnight. The reaction mixture is added to ice water, made alkaline with sodium hydroxide and extracted with tert.-butylmethylether. The organic phases are washed with water, dried and evaporated down. Then the residue is purified by chromatography.

Yield: 1.9 g (22%); mass spectroscopy: [M+H]⁺=218.

d) 8-{2-[1,1-dimethyl-2-(3-trifluoromethyl-phenyl)-ethylamino]-1-hydroxy-ethyl}-6-hydroxy-4H-benzo[1,4]oxazin-3-one 357 mg (1 mmol) 6-benzyloxy-8-(2-ethoxy-2-hydroxy-acetyl)-4H-benzo[1,4]oxazin-3-one and 217 mg (1 mmol)

1,1-dimethyl-2-(3-trifluoromethyl-phenyl)-ethylamine are stirred for 3 hours in 5 mL ethanol at 65° C. The mixture is cooled to ambient temperature, 113 mg (3 mmol) of sodium borohydride are added and the mixture is stirred overnight. It is combined with 2 mL water, stirred for 30 minutes and then diluted with 10 mL dichloromethane. The solution is filtered through kieselguhr and washed with dichloromethane. The eluate is freed from solvent and the residue is dissolved in 5 mL ethanol and hydrogenated at 2.5 bar and ambient temperature with palladium on charcoal (10%) as catalyst. Then the catalyst is separated off and the crude product is purified by chromatography (reverse phase, acetonitrile/water gradient with 0.1% trifluoroacetic acid). Beige solid. Yield: 169 mg (31%, trifluoroacetate); mass spectroscopy: [M+H]$^+$=425.

EXAMPLE 4

8-{2-[1,1-dimethyl-2-(4-trifluoromethoxy-phenyl)-ethylamino]-1-hydroxy-ethyl}-6-hydroxy-4H-benzo[1,4]oxazin-3-one

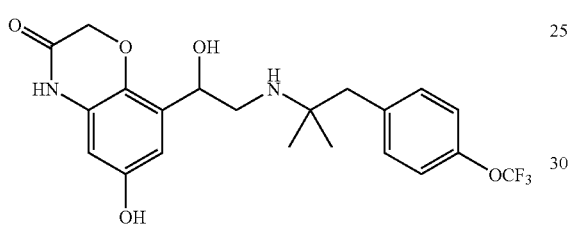

a) 2-methyl-1-(4-trifluoromethoxy-phenyl)-propan-1-ol

The target compound is obtained analogously to method described for Example 1a). First of all a Grignard is prepared from 23.7 g (96 mmol) 1-bromo-4-(trifluoromethoxy)-benzene and 2.35 g (97 mmol) magnesium, which is then reacted with 7.3 g (100 mmol) isobutyraldehyde. After working up and purification by column chromatography 14.8 g of a brown oil are obtained which is further reacted directly.

b) 1-(2-methyl-propenyl)-4-trifluoromethoxy-benzene 14.8 g (63 mmol) 2-methyl-1-(4-trifluoromethoxy-phenyl)-propan-1-ol are reacted and worked up as described in the method for Example 1b).

Yield: 9.8 g (72%); mass spectroscopy: [M]$^+$=216.

c) N-[1,1-dimethyl-2-(4-trifluoromethoxy-phenyl)-ethyl]-formamide

A Ritter reaction with 9.8 g (45 mmol) 1-(2-methyl-propenyl)-4-trifluoromethoxy-benzene, carried out as described for Example 1c), yields 7.8 g of slightly contaminated product. Mass spectroscopy: [M+H]$^+$=262.

d) 1,1-dimethyl-2-(4-trifluoromethoxy-phenyl)-ethylamine 7.8 g (30 mmol) N-[1,1-dimethyl-2-(4-trifluoromethoxy-phenyl)-ethyl]-formamide and 3.5 g potassium hydroxide are stirred overnight at 140° C. in 30 mL ethyleneglycol. After cooling to ambient temperature the reaction mixture is diluted with water and extracted with dichloromethane. The combined organic phases are washed with water, dried with sodium sulphate and evaporated down. The oil remaining is purified through a short silica gel column (dichloromethane/methanol/ammonia=90/10/1).

Yield: 4.0 g (57%); mass spectroscopy: [M+H]$^+$=234.

e) 8-{2-[1,1-dimethyl-2-(4-trifluoromethoxy-phenyl)-ethylamino]-1-hydroxy-ethyl}-6-hydroxy-4H-benzo[1,4]oxazin-3-one The target compound is obtained by reacting 357 mg (1 mmol) 6-benzyloxy-8-(2-ethoxy-2-hydroxy-acetyl)-4H-benzo[1,4]oxazin-3-one with 233 mg (1 mmol) 1,1-dimethyl-2-(4-trifluoromethoxy-phenyl)-ethylamine using the method described for Example 2c). Beige solid. Yield: 279 mg (50%, trifluoroacetate); mass spectroscopy: [M+H]$^+$=441.

EXAMPLE 5

8-{2-[2-(4-chloro-3-trifluoromethyl-phenyl)-1,1-dimethyl-ethylamine]-1-hydroxy-ethyl}-6-hydroxy-4H-benzo[1,4]oxazin-3-one

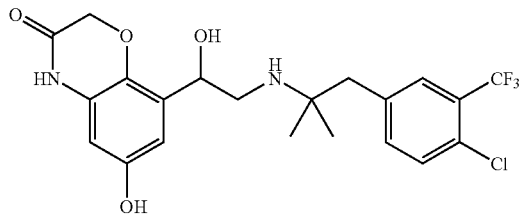

a) 1-(4-chloro-3-trifluoromethyl-phenyl)-2-methyl-propan-1-ol

Prepared analogously to the method described for Example 1a) from 2.3 mL (15 mmol) of 5-bromo-2-chlorobenzotrifluoride and 1.3 mL (14 mmol) isobutyraldehyde. Yellow oil. Yield: 2.0 g (53%).

b) 1-chloro-4-(2-methyl-propenyl)-2-trifluoromethyl-benzene 1.50 g (5.9 mmol) 1-(4-chloro-3-trifluoromethyl-phenyl)-2-methyl-propan-1-ol and 0.50 g (2.6 mmol) p-toluenesulphonic acid monohydrate in 50 mL toluene are refluxed for 3 hours using the water separator. After working up analogously to Example 1b) a brown oil is obtained. Yield: 1.4 g; mass spectrometry: [M]$^+$=234/6.

c) N-[2-(4-chloro-3-trifluoromethyl-phenyl)-1,1-dimethyl-ethyl-formamide

A Ritter reaction with 1.30 g (5.5 mmol) 1-chloro-4-(2-methyl-propenyl)-2-trifluoromethyl-benzene using the process described for Example 1c) yields the target compound in the form of a brown oil.

Yield: 1.50 g (97%); mass spectrometry: [M+H]$^+$=280/2.

d) 2-(4-chloro-3-trifluoromethyl-phenyl)-1,1-dimethyl-ethylamine

Prepared analogously to Example 1d) from 1.50 g (5.4 mmol) N-[2-(4-chloro-3-trifluoromethyl-phenyl)-1,1-dimethyl-ethyl-formamide. Brown oil.

Yield: 1.19 g (88%); mass spectrometry: [M+H]$^+$=252/4.

e) 6-benzyloxy-8-{2-[2-(4-chloro-3-trifluoromethyl-phenyl)-1,1-dimethyl-ethylamine]-1-hydroxy-ethyl}-4H-benzo[1,4]oxazin-3-one 357 mg (1 mmol) 6-benzyloxy-8-(2-ethoxy-2-hydroxy-acetyl)-4H-benzo[1,4]oxazin-3-one and 252 mg (1 mmol) 2-(4-chloro-3-trifluoromethyl-phenyl)-1,1-dimethyl-ethylamine are reacted and worked up analogously to the method described for Example 2c). The final purification is carried out by chromatography. Beige solid.

Yield: 316 mg (48%, trifluoroacetate); mass spectrometry: [M+H]$^+$=549/51.

f) 8-{2-[2-(4-chloro-3-trifluoromethyl-1-phenyl)-1,1-dimethyl-ethylamine]-1-hydroxy-ethyl}-6-hydroxy-4H-benzo[1,4]oxazin-3-one 316 mg (0.48 mmol) 6-benzyloxy-8-{2-[2-(4-chloro-3-trifluoromethyl-phenyl)-1,1-dimethyl-ethylamine]-1-hydroxy-ethyl}-4H-benzo[1,4]oxazin-3-one are dissolved in 3 mL dichloromethane and cooled to –40° C. At this temperature 1.4 mL of a 1 molar solution of boron tribromide in dichloromethane are added. After 10 minutes the reaction is stopped by the addition of dichloromethane and water and the solution is filtered through kieselguhr. The filtrate is freed from solvents and the residue is chromatographed (reverse phase; water/acetonitrile gradient with 0.1% trifluoroacetic acid). Pink solid.

Yield: 49 mg (18%, trifluoroacetate); mass spectroscopy [M+H]$^+$=459/61.

EXAMPLE 6

8-{2-[1,1-dimethyl-2-(2-trifluoromethyl-phenyl)-ethylamino]-1-hydroxy-ethyl}-6-hydroxy-4H-benzo[1,4]oxazin-3-one

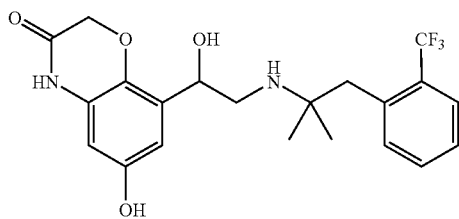

a) 1-(4-chloro-2-trifluoromethyl-phenyl)-2-methyl-propan-1-ol

A Grignard is prepared from 1.77 g (73 mmol) of iodine-activated magnesium and 18.70 g (72 mmol) 1-bromo-4-chloro-2-trifluoromethyl-benzene dissolved in 150 mL diethyl ether. 5.46 g (72 mmol) isobutyraldehyde in 30 mL diethyl ether are added dropwise to the Grignard reagent at ambient temperature. After the addition has ended the reaction mixture is refluxed for 30 minutes and then stirred overnight at ambient temperature. It is combined with ice water and acidified with hydrochloric acid. The aqueous phase is separated off and extracted with diethyl ether. The organic phases are combined, dried with sodium sulphate and evaporated down. The residue is chromatographed on a silica gel column (petroleum ether/ethyl acetate=9:1). 10.5 g of oil.

b) 4-chloro-1-(2-methyl-propenyl)-2-trifluoromethyl-benzene 8.00 g (42 mmol) 1-(4-chloro-2-trifluoromethyl-phenyl)-2-methyl-propan-1-ol and 2.5 g p-toluenesulphonic acid monohydrate in 200 mL toluene are refluxed overnight, while the water formed is captured using a water separator. The reaction mixture is left to cool, combined with water and the organic phase is separated off. It is extracted with toluene and the organic phases are combined and evaporated down. The residue is added to a short silica gel column and eluted with hexane. Colourless oil.

Yield: 6.1 g (63%); mass spectroscopy [M]$^+$=234/6.

c) N-[2-(4-chloro-2-trifluoromethyl-phenyl)-1,1-dimethyl-ethyl]-formamide

Using the process described for Example 1c) 5.9 g (25 mmol) 4-chloro-1-(2-methyl-propenyl)-2-trifluoromethyl-benzene are reacted in a Ritter-reaction and worked up. Yellow oil. Yield: 5.7 g (81%); mass spectroscopy [M+H]$^+$=280/2.

d) 2-(4-chloro-2-trifluoromethyl-phenyl)-1,1-dimethyl-ethylamine 5.70 g (20 mmol) N-[2-(4-chloro-2-trifluoromethyl-phenyl)-1,1-dimethyl-ethyl]-formamide and 3.00 g potassium hydroxide are stirred overnight at 140° C. in 20 mL ethyleneglycol. The reaction mixture is combined with water and repeatedly extracted with dichloromethane. The combined organic phases are washed with water, dried with sodium sulphate and evaporated down. The residue is filtered through a short column containing silica gel (eluant: dichloromethane/methanol/ammonia=9:1:0.1).

Yield: 3.7 g (51%); mass spectroscopy [M+H]$^+$=252/4.

e) 8-{2-[1,1-dimethyl-2-(2-trifluoromethyl-phenyl)-ethylamino]-1-hydroxy-ethyl}-6-hydroxy-4H-benzo[1,4]oxazin-3-one 357 mg (1 mmol) 6-benzyloxy-8-(2-ethoxy-2-hydroxy-acetyl)-4H-benzo[1,4]oxazin-3-one and 252 mg (1 mmol) 2-(4-chloro-2-trifluoromethyl-phenyl)-1,1-dimethyl-ethylamine are reacted and worked up analogously to the method described for Example 2c). White solid. Yield: 165 mg (31%, trifluoroacetate); mass spectroscopy [M+H]$^+$=425.

EXAMPLE 7

8-{2-[2-(3,5-bis-trifluoromethyl-phenyl)-1,1-dimethyl-ethylamino]-1-hydroxy-ethyl}-6-hydroxy-4H-benzo[1,4]oxazin-3-one

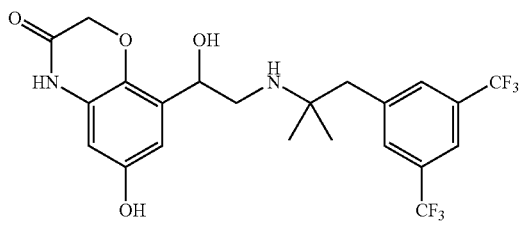

a) 1-(2-methyl-propenyl)-3,5-bis-trifluoromethyl-benzene 15.88 g (36 mmol) isopropyltriphenylphosphonium iodide are dissolved in 210 mL diethyl ether/tetrahydrofuran (1:1) and cooled to −10° C. At this temperature 25 mL of a 1.6 molar solution of butyllithium in hexane are added dropwise. Then the mixture is stirred for 3 h at ambient temperature and then cooled to −50° C. 9.98 g (40 mmol) of 3,5-bis-trifluoromethyl-benzaldehyde dissolved in 15 ml of tetrahydrofuran are added dropwise and the mixture is stirred overnight while heating to ambient temperature. The reaction mixture is combined with water and hexane, stirred for 30 minutes and then filtered. The organic phase is separated off, washed repeatedly with water, dried with sodium sulphate and evaporated down. The residue is purified by chromatography on a short silica gel column (hexane/ethyl acetate=50:1). Yellow oil.

Yield: 4.50 g (42%); mass spectroscopy $[M]^+=268$.

b) N-[2-(3,5-bis-trifluoromethyl-phenyl)-1,1-dimethyl-ethyl]-formamide

The target compound is obtained by reacting 4.29 g (16 mmol) 1-(2-methyl-propenyl)-3,5-bis-trifluoromethyl-benzene using the process described for Example 1c). In a departure from this process, the crude product is additionally filtered again at the end through a short silica gel column (eluant: dichloromethane/methanol/ammonia=9:1:0.1). Beige solid. Yield: 1.00 g (20%); mass spectroscopy $[M+H]^+=314$.

c) 2-(3,5-bis-trifluoromethyl-phenyl)-1,1-dimethyl-ethylamine

Prepared analogously to process described for Example 1d) from 1.40 g (4.4 mmol) N-[2-(3,5-bis-trifluoromethyl-phenyl)-1,1-dimethyl-ethyl]-formamide. Brown oil.

Yield: 0.60 g (47%); mass spectroscopy $[M+H]^+=286$.

d) 8-{2-[2-(3,5-bis-trifluoromethyl-phenyl)-11-dimethyl-ethylamino]-1-hydroxy-ethyl}-6-hydroxy-benzo[1,4]oxazin-3-one Prepared from 357 mg (1 mmol) 6-benzyloxy-8-(2-ethoxy-2-hydroxy-acetyl)-4H-benzo[1,4]oxazin-3-one and 285 mg (1 mmol) 2-(3,5-bis-trifluoromethyl-phenyl)-1,1-dimethyl-ethylamine analogously to the method described for Example 2c). In a departure from this process, the hydrogenation is carried out using Raney nickel. After the catalyst has been removed by suction filtration the filtrate is evaporated down and the residue is filtered through a short silica gel column (eluant: dichloromethane/methanol=9:1). The fractions containing the product are freed from solvent and stirred in water/acetonitrile. Brown solid.

Yield: 7 mg (2%); mass spectroscopy $[M+H]^+=493$.

The (R)- and (S)-enantiomers of the above-mentioned Examples may be obtained by separating the racemates analogously to common methods known in the art.

The compounds of general formula 1 may be used on their own or combined with other active substances of formula 1 according to the invention. The compounds of general formula 1 may optionally also be combined with other pharmacologically active substances. These include, in particular, anticholinergics, optionally other betamimetics, antiallergic agents, PDE-IV inhibitors, PAF-antagonists, leukotriene-antagonists, EGFR inhibitors and corticosteroids and combinations of these active substances.

Examples of preferred anticholinergics which may be mentioned include ipratropium, oxitropium and tiotropium salts. Pharmaceutical combinations which contain the abovementioned salts, in addition to the compounds of formula 1 according to the invention, preferably contain those salts of ipratropium, oxitropium or tiotropium wherein the anion is selected from among the chloride, bromide, iodide, sulphate, phosphate, methanesulphonate, nitrate, maleate, acetate, citrate, fumarate, tartrate, oxalate, succinate, benzoate and p-toluenesulphonate, optionally in the form of one of the solvates or hydrates thereof.

Within the scope of the present invention, the corticosteroids which may optionally be used in conjunction with the compounds of formula 1 may be compounds selected from among flunisolide, beclomethasone, triamcinolone, budesonide, fluticasone, mometasone, ciclesonide, rofleponide and dexamethasone. In some cases, within the scope of the present patent application, the term steroids is used on its own instead of the word corticosteroids. Any reference to steroids within the scope of the present invention includes a reference to salts or derivatives which may be formed from the steroids. Examples of possible salts or derivatives include: sodium salts, sulphobenzoates, phosphates, isonicotinates, acetates, propionates, dihydrogen phosphates, palmitates, pivalates or furoates. In some cases the corticosteroids may also occur in the form of their hydrates.

Within the scope of the present invention, the term dopamine agonists, which may optionally be used in conjunction with the compounds of formula 1, denotes compounds selected from among bromocriptine, cabergolin, alpha-dihydroergocryptine, lisuride, pergolide, pramipexol, roxindol, ropinirol, talipexol, tergurid and viozan. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of antiallergic agents which may be used according to the invention as a combination with the compound of formula 1 include epinastin, cetirizin, azelastin, fexofenadin, levocabastin, loratadine, mizolastin, ketotifen, emedastin, dimetinden, clemastine, bamipin, cexchloropheniramine, pheniramine, doxylamine, chlorophenoxamine, dimenhydrinate, diphenhydramine, promethazine, ebastin, desloratidine and meclizine. Any reference to the abovementioned antiallergic agents also includes, within the scope of the present invention, a reference to any pharmacologically acceptable acid addition salts thereof which may exist.

Examples of PDE-IV inhibitors which may be used according to the invention as a combination with the compound of formula 1 include compounds selected from among enprofylline, roflumilast, ariflo, Bay-198004, CP-325,366, BY343, D-4396 (Sch-351591), V-11294A and AWD-12-281. Any reference to the abovementioned PDE-IV inhibitors also includes, within the scope of the present invention, a reference to any pharmacologically acceptable acid addition salts thereof which may exist. By the physiologically acceptable acid addition salts which may be formed by the abovementioned PDE-IV inhibitors are meant, for example, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid. According to the invention, the salts selected from among the acetate, hydrochloride, hydrobromide, sulphate, phosphate and methanesulphonate are preferred in this context.

Examples of EGFR kinase inhibitors which may be used as a combination with the compounds of formula 1 according to the invention include, in particular, compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, and 4-[(3-chloro-4-flouro-phenyl-amino-]-6-{1-[(2-methoxyethyl)carbonyl]-piperidin-4-yloxy}-7-methoxy-quinazoline. Any reference to the abovementioned EGFR kinase inhibitors also includes, within the scope of the present invention, a reference to any pharmacologically acceptable acid addition salts thereof which may exist. By the physiologically acceptable acid addition salts thereof which may be formed by the above-mentioned EGFR inhibitors are meant, according to the invention, pharmaceutically acceptable salts selected from among the salts of hydrochloric acid, hydrobromic acid, sulphuric acid, phosphoric acid, methanesulphonic acid, acetic acid, fumaric acid, succinic acid, lactic acid, citric acid, tartaric acid or maleic acid. The salts selected from among the acetate, hydrochloride, hydrobromide, sulphate, phosphate and methanesulphonate are preferred according to the invention.

Suitable preparations for administering the compounds of formula 1 include for example tablets, capsules, suppositories, solutions and powders etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatin and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

For administering the compounds of formula 1 for the treatment of COPD it is particularly preferred according to the invention to use preparations or pharmaceutical formulations which are suitable for inhalation. Inhalable preparations include inhalable powders, propellant-containing metered-dose aerosols or propellant-free inhalable solutions. Within the scope of the present invention, the term propellant-free inhalable solutions also includes concentrates or sterile inhalable solutions ready for use. The formulations which may be used within the scope of the present invention are described in more detail in the next part of the specification.

The inhalable powders which may be used according to the invention may contain 1 either on its own or in admixture with suitable physiologically acceptable excipients. If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 µm. It may sometimes seem appropriate to add finer excipient fractions with an average particle size of 1 to 9 µm to the excipient mentioned above. These finer excipients are also selected from the group of possible excipients listed hereinbefore. Finally, in order to prepare the inhalable powders according to the invention, micronised active substance 1, preferably with an average particle size of 0.5 to 10 µm, more preferably from 1 to 5 µm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed.

The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The abovementioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred. Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the µg range. The compounds of formula 1 may also be used effectively above the µg range. The dosage may then be in the gram range, for example.

In another aspect the present invention relates to the above-mentioned pharmaceutical formulations as such which are characterised in that they contain a compound of formula 1, particularly the above-mentioned pharmaceutical formulations which can be administered by inhalation.

The following examples of formulations illustrate the present invention without restricting its scope:

Examples of Pharmaceutical Formulations

| A) Tablets | per tablet |
|---|---|
| active substance 1 | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose and some of the maize starch are mixed together. The mixture is screened, then moistened with a solution of polyvinylpyrrolidone in water, kneaded, wet granulated and dried. The granules, the remaining maize starch and the magnesium stearate are screened and mixed together. The mixture is pressed into tablets of suitable shape and size.

| B) Tablets | per tablet |
|---|---|
| active substance 1 | 80 mg |
| lactose | 55 mg |
| maize starch | 190 mg |
| microcrystalline cellulose | 35 mg |
| polyvinylpyrrolidone | 15 mg |
| sodium carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) | Ampoule solution | |
|---|---|---|
| | active substance 1 | 50 mg |
| | sodium chloride | 50 mg |
| | water for inj. | 5 ml |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilised and heat-sealed. The ampoules contain 5 mg, 25 mg and 50 mg of active substance.

| D) | Metering aerosol | |
|---|---|---|
| | active substance 1 | 0.005 |
| | sorbitan trioleate | 0.1 |
| | monofluorotrichloromethane and TG134a:TG227 2:1 | ad 100 |

The suspension is transferred into a conventional aerosol container with metering valve. Preferably 50 µl suspension are released on each actuation. The active substance may also be released in higher doses if desired (e.g. 0.02 wt.-%).

| E) | Solutions (in mg/100 ml) | |
|---|---|---|
| | active substance 1 | 333.3 mg |
| | benzalkonium chloride | 10.0 mg |
| | EDTA | 50.0 mg |
| | HCl (1N) | ad pH 3.4 |

This solution can be prepared in the usual way.

| F) | Inhalable powder | |
|---|---|---|
| | active substance 1 | 12 µg |
| | lactose monohydrate | ad 25 mg |

The inhalable powder is prepared in the usual way by mixing the individual ingredients.

The invention claimed is:

1. A compound of formula 1

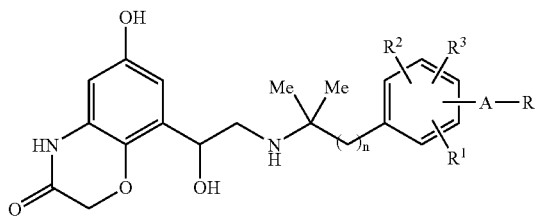

1 wherein
n denotes 1 or 2;
A denotes oxygen or a single bond;
R denotes —$C_1$-$C_6$-alkyl, which is mono- or polysubstituted by one or more halogen atoms;
$R^1$, $R^2$ and $R^3$ which may be identical or different denote hydrogen, $C_1$-$C_6$-alkyl, halogen-$C_1$-$C_6$-alkylene, OH, HO—$C_{1-6}$-alkylene, —O—$C_1$-$C_6$-alkyl, $C_6$-$C_{10}$-aryl, $C_6$-$C_{10}$-aryl-$C_1$-$C_4$-alkylene, $C_6$-$C_{10}$-aryl-$C_1$-$C_6$-alkylene-O, —COOH, —COO$C_1$-$C_6$-alkyl, —O—$C_1$-$C_6$-alkylene-COOH, —O—$C_1$-$C_6$-alkylene-COO$C_1$-$C_6$-alkyl, —NHSO$_3$H, —NHSO$_2$—$C_1$-$C_6$-alkyl, CN, NH$_2$, —NH—$C_1$-$C_6$-alkyl, —N($C_1$-$C_6$-alkyl)$_2$, NO$_2$, —S—$C_1$-$C_6$-alkyl, —SO$_2$—$C_1$-$C_6$-alkyl, —SO—$C_1$-$C_6$-alkyl, —O(CO)$C_1$-$C_6$-alkyl, —CO$C_1$-$C_6$-alkyl, —NHCO$C_1$-$C_6$-alkyl or halogen;
or an acid addition salt thereof with a pharmacologically acceptable acid.

2. The compound of formula 1 according to claim 1, wherein
n denotes 1 or 2;
A denotes oxygen or a single bond;
R denotes $C_1$-$C_4$-alkyl, which is mono- to trisubstituted, by one or more halogen atoms;
$R^1$, $R^2$ and $R^3$ which may be identical or different denote hydrogen, $C_1$-$C_4$-alkyl, halogen-$C_1$-$C_4$-alkylene, OH, HO—$C_1$-$C_4$-alkylene, —O—$C_1$-$C_4$-alkyl, phenyl, phenyl-$C_1$-$C_4$-alkylene, phenyl-$C_1$-$C_4$-alkylene-O, —COOH, —COO$C_1$-$C_4$-alkyl, —O—$C_1$-$C_4$-alkylene-COOH, —O—$C_1$-$C_4$-alkylene-COO$C_1$-$C_4$-alkyl, —NHSO$_2$—$C_1$-$C_4$-alkyl, CN, NH$_2$, —NH—$C_1$-$C_4$-alkyl, —N($C_1$-$C_4$-alkyl)$_2$, NO$_2$, —S—$C_1$-$C_4$-alkyl, —SO$_2$—$C_1$-$C_4$-alkyl, —SO—$C_1$-$C_4$-alkyl, —O(CO)$C_1$-$C_4$-alkyl, —CO$C_1$-$C_4$-alkyl, —NHCO$C_1$-$C_4$-alkyl or halogen.

3. The compound of formula 1 according to claim 1, wherein
n denotes 1 or 2,
A denotes oxygen or a single bond;
R denotes a methyl or ethyl group which is mono-, di- or trisubstituted by one or more halogen atoms selected from fluorine or chlorine;
$R^1$ and $R^2$ which may be identical or different denote hydrogen, halogen, $C_1$-$C_4$-alkyl or —O—$C_1$-$C_4$-alkyl; and
$R^3$ denotes hydrogen, $C_1$-$C_4$-alkyl, OH, halogen, —O—$C_1$-$C_4$-alkyl, halogen-$C_1$-$C_4$-alkylene, —O—$C_1$-$C_4$-alkylene-COOH, or —O—$C_1$-$C_4$-alkylene-CO—O—$C_1$-$C_4$-alkyl.

4. The compound of formula 1 according to claim 1, wherein
n denotes 1;
A denotes oxygen or a single bond;
R denotes —CH$_2$-CH$_2$Cl, —CH$_2$CCl$_3$, —CHCl—CCl$_3$, —CCL$_3$, —CH$_2$Cl, —CHCl$_2$, —CH$_2$CF$_3$, —CHF—CF$_3$, —CF$_3$, —CH$_2$F, —CH$_2$-CH$_2$F or —CHF$_2$;
$R^1$ and $R_2$ which may be identical or different denote hydrogen, fluorine, chlorine, methyl or methoxy; and
$R^3$ denotes hydrogen, $C_1$-$C_4$-alkyl, OH, fluorine, chlorine, bromine, —O—$C_1$-$C_4$-alkyl, —CF$_3$, —O—$C_1$-$C_4$-alkylene-COOH or —O—$C_1$-$C_4$-alkylene-CO—O—$C_1$-$C_4$-alkyl.

5. The compound of formula 1 according to claim 1, wherein
n denotes 1;
A denotes oxygen or a single bond;
R denotes —CH$_2$CF$_3$, —CHF—CF$_3$, —CF$_3$, —CH$_2$F, —CH$_2$—CH$_2$F or —CHF$_2$;
$R^1$ and $R^2$ which may be identical or different denote hydrogen, fluorine, chlorine, methyl or ethyl; and $R^3$ denotes hydrogen, fluorine, chlorine, methyl, ethyl, OH, methoxy, ethoxy, —CF$_3$, —O—CH$_2$—COOH, —O—CH$_2$—COOmethyl or —O—CH$_2$—COOethyl.

6. The compound of formula 1 according to claim 1, wherein the compound of formula 1 is in the form of an individual optical isomer, mixtures of the individual enantiomers or racemates thereof.

7. The compound of formula 1 according to claim 1, wherein the compound of formula 1 is in the form of an acid addition salt thereof with a pharmacologically acceptable acid.

8. A pharmaceutical composition comprising the compound of formula 1 according to claim 1 or a pharmaceutically acceptable acid addition salt therof and a pharmaceutically acceptable excipient.

9. The pharmaceutical composition according to claim 8, which is in a form suitable for inhalation.

10. The pharmaceutical composition according to claim 9, wherein the form suitable for inhalation is selected from the group consisting of inhalable powders, propellant-driven metering aerosols and propellant-free inhalable solutions.

11. The compound of formula 1 according to claim 1, wherein:
$R^1$ and $R^2$ denote hydrogen.

12. The compound of formula 1 according to claim 1, wherein:
A denotes a single bond.

13. The compound of formula 1 according to claim 1, wherein:
$R^3$ denotes hydrogen, fluorine, chlorine, methyl, ethyl, OH, ruethoxy or ethoxy.

14. The compound of formula 1 according to claim 1, wherein:
R denotes —CF$_3$, —CH$_2$F or —CHF$_2$.

15. The compound of formula 1 according to claim 1, wherein the compound is:
- 8-{2-[2-(4-fluoro-3-trifluoromethyl-phenyl)-1,1-dimethyl-ethylamino]-1-hydroxy-ethyl}-6-hydroxy-4H-benzo [1,4]oxazin-3-one;
- 8-{2-[1,1-dimethyl-2-(4-trifluoromethyl-phenyl)-ethylamino]-1-hydroxy-ethyl}-6-hydroxy-4H-benzo[1,4] oxazin-3-one;
- 8-{2-[1,1-dimethyl-2-(3-trifluomethyl-phenyl)-ethylamino]-1-hydroxy-ethyl}-6-hydroxy-4H-benzo[1,4] oxazin-3-one;
- 8-{2-[1,1-dimethyl-2-(4-trifluoromethoxy-phenyl)-ethylamino]-1-hydroxy-ethyl}-6-hydroxy-4H-benzo[1,4] oxazin-3-one;
- 8-{2-[2-(4-chloro-3-trifluoroethyl-phenyl)-1,1-dimethyl-ethylamine]-1-hydroxy-ethyl}-6-hydroxy-4H-benzo[1, 4]oxazin-3-one;
- 8-{2-[1,1-dimethyl-2-(2-trifluoromethyl-phenyl)-ethylamino]-1-hydroxy-ethyl}-6-hydroxy-4H-benzo[1,4] oxazin-3-one; or
- 8-{2-[2-(3,5-bis-trifluoromethyl-phenyl)-1,1-dimethyl-ethylamino]-1-hydroxy-ethyl}-6-hydroxy-4H-benzo[1, 4]oxazin-3-one.

16. The compound of formula 1 according to claim 1, wherein the compound is in the form of an enantiomerically pure R-enantiomer of the compound.

* * * * *